(12) United States Patent
Huot et al.

(10) Patent No.: US 11,759,336 B2
(45) Date of Patent: Sep. 19, 2023

(54) PROSTHETIC FOOT

(71) Applicant: CICR Comité International de la Croix-Rouge, Geneva (CH)

(72) Inventors: Grégory Huot, Lutry (CH); Mathieu Janier, Pully (CH); Rajasundar Chandran, Ecublens (CH); Mathieu Falbriard, Vendlincourt (CH); Thierry Patrick Barras, Gilly (CH); Michael Rechsteiner, Avully/GE (CH); Marc Zlot, Berne (CH)

(73) Assignee: Comité International de la Croix-Rouge (CICR), Geneva (CH)

( * ) Notice: Subject to any disclaimer, the term of this patent is extended or adjusted under 35 U.S.C. 154(b) by 21 days.

(21) Appl. No.: 17/057,944

(22) PCT Filed: Jul. 8, 2019

(86) PCT No.: PCT/IB2019/055785
§ 371 (c)(1),
(2) Date: Nov. 23, 2020

(87) PCT Pub. No.: WO2020/012319
PCT Pub. Date: Jan. 16, 2020

(65) Prior Publication Data
US 2021/0298924 A1     Sep. 30, 2021

(30) Foreign Application Priority Data
Jul. 10, 2018   (WO) ................. PCT/IB2018/055071

(51) Int. Cl.
*A61F 2/66* (2006.01)
(52) U.S. Cl.
CPC .............. *A61F 2/66* (2013.01); *A61F 2/6607* (2013.01)

(58) Field of Classification Search
CPC ................................ A61F 2/66; A61F 2/6607
See application file for complete search history.

(56) References Cited

U.S. PATENT DOCUMENTS

| 4,645,509 A | 2/1987 | Poggi et al. |
| 4,652,266 A | 3/1987 | Truesdell |
(Continued)

FOREIGN PATENT DOCUMENTS

| CA | 2103341 A1 | 4/1995 |
| EP | 0648479 A1 | 4/1995 |

OTHER PUBLICATIONS

B.L Kalasson, Carbon fibre and fibre lamination in prosthetics and orthotics: some basic theory and practical advice for the practitioner, (1995).*

(Continued)

*Primary Examiner* — Bruce E Snow
(74) *Attorney, Agent, or Firm* — Nixon & Vanderhye P.C.

(57) ABSTRACT

A prosthetic foot comprising an internal keel (1) and an encapsulation material (2). The keel (1) is made of two parts (3,4), namely an elastic ankle (3) and an elastic blade (4), to ensure a behaviour of the prosthesis as close as possible to the biomechanics of a sound human foot (plantar flexion, dorsiflexion, inversion, eversion). The materials and design used for the keel (1) allow storing and releasing strain energy at the right phases of the gait cycle. Elastomeric foams act as safety features in specific areas to prevent keel overloading. The keel (1) is preferably encapsulated into two types of foam to fill internal space and as cosmetic feature as it has a human foot shape.

20 Claims, 2 Drawing Sheets

(56) References Cited

U.S. PATENT DOCUMENTS

| | | | | |
|---|---|---|---|---|
| 5,037,444 A * | 8/1991 | Phillips | ...................... | A61F 2/66 |
| | | | | 623/53 |
| 5,116,385 A | 5/1992 | Allard et al. | | |
| 5,156,632 A | 10/1992 | Wellershaus | | |
| 5,976,191 A * | 11/1999 | Phillips | ...................... | A61F 2/66 |
| | | | | 623/55 |
| 6,197,066 B1 * | 3/2001 | Gabourie | ................... | A61F 2/66 |
| | | | | 623/55 |
| 6,743,260 B2 | 6/2004 | Townsend et al. | | |
| 7,771,488 B2 * | 8/2010 | Asgeirsson | ............... | A61F 2/66 |
| | | | | 623/55 |
| 9,011,554 B2 * | 4/2015 | Rubie | ....................... | A61F 2/66 |
| | | | | 623/55 |
| 2006/0229736 A1 | 10/2006 | Christensen | | |
| 2010/0023135 A1 | 1/2010 | Rubie et al. | | |
| 2012/0303135 A1 * | 11/2012 | Vo | .............................. | A61F 2/64 |
| | | | | 623/33 |
| 2017/0049584 A1 * | 2/2017 | Pusch | ....................... | A61F 2/66 |

OTHER PUBLICATIONS

Amputee Coalition, Prosthetic Feet Fact Sheet Updated (Jun. 2018).*
International Search Report for PCT/IB2019/055785 dated Nov. 6, 2019, 5 pages.
Written Opinion of the ISA for PCT/IB2019/055785 dated Nov. 6, 2019, 6 pages.

* cited by examiner

PROSTHETIC FOOT

This application is the U.S. national phase of International Application No. PCT/IB2019/055785 filed Jul. 8, 2019 which designated the U.S. and claims priority to International Application No. PCT/IB2018/055071 filed Jul. 10, 2018, the entire contents of each of which are hereby incorporated by reference.

FIELD OF INVENTION

The invention relates to a prosthetic foot comprising a keel embedded in a material, e.g. a foam.

STATE OF THE ART

Examples of such prosthetic feet are disclosed in the following patent documents: EP 0 648 479 A1, U.S. Pat. No. 5,116,385, 4,645,509 or 5,156,632.

GENERAL DESCRIPTION OF THE INVENTION

The object of the present invention is to provide a prosthetic foot having improved biomechanical properties.

The prosthetic foot according to the invention is defined in the claims.

It comprises a keel embedded in an encapsulation material; said keel comprising a U-shaped elastic ankle, preferably made of an injection-moulded LFT composite, and an elastic blade that is fixed to the bottom part of the ankle element, said encapsulation material may advantageously comprise an internal foam that at least partially encapsulates the keel and an external foam that encapsulates the internal foam, the external foam having a higher density than the internal foam density.

Biomechanically, the prosthetic foot according to the invention provides biomechanics that is very similar to the one of a sound human foot (plantar flexion, dorsiflexion, inversion, eversion). The materials and design used for the keel allow storing and releasing strain energy at the right phases of the gait cycle. The encapsulation material acts as a safety feature to prevent keel overloading and as cosmetic feature as it has a human foot shape.

The LFT composite preferably comprises 15% to 70% volume fraction of fibres with a length ranging from 1 mm to 15 mm.

The elastic blade may advantageously be made of a composite that comprises 40% to 65% volume fraction of fibres which are typically longer than 50 mm.

In a preferred embodiment, at least an important part of the ankle element is encapsulated in low density foam (typically <0.7 g/cm$^3$), said foam being overmoulded by injection moulding, casted or glued using an adhesive.

In a preferred embodiment according to the invention the prosthetic foot includes an overload protection system to prevent damage of the prosthetic foot in case of severe loading during use. The overload protection system includes at least one spacer, preferably made of an elastomeric material, that is arranged between two overlapping parts of the keel 1.

The prosthetic foot is designed in a way it can be bolted to a prosthetic leg from the sole surface and through its whole internal structure like most SACH (Solid Ankle Cushion Heel) feet available on the market.

DETAILED DESCRIPTION OF THE INVENTION

The invention will be better understood in the present chapter, with a non-limiting example illustrated by the following figures.

NUMERICAL REFERENCES USED IN THE FIGURES

Figure 1:
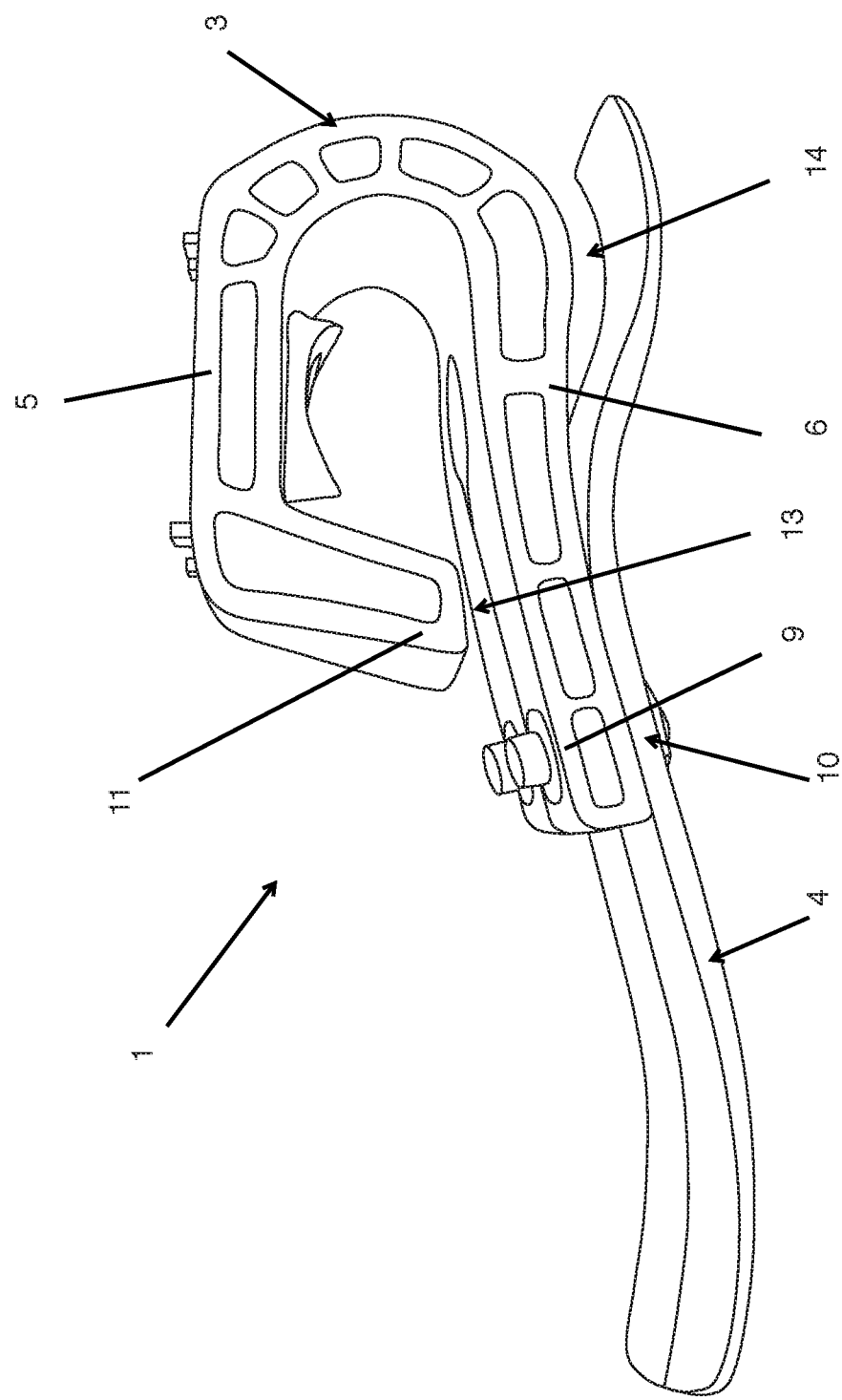
FIG. 1 shows a keel according to the invention

1. Keel
2. Encapsulation material
3. Ankle
4. Elastic blade
5. Ankle upper branch
6. Ankle lower branch
7. Forefoot
8. Foot bottom
9. Lower branch free end
10. Blade central area
11. Protection system element
12. Heel
13. 1$^{st}$ overload protection area
14. 2$^{nd}$ overload protection area
15. Shell The keel 1 (see both figures) is essentially made of two elements, namely:

An elastic partly slotted ankle 3 made of an injection-moulded thermoplastic composite including 15% to 70% volume fraction of fibres with a length preferably ranging from 1 mm to 15 mm, the fibres being usually carbon fibres or glass fibres. The composite thermoplastic matrix may be composed of a thermoplastic polymer matrix such as, but not limited to PE, PA, PP, PEI, PEKK, PEEK, PET, PI, ABS, POM, PMMA, PPA, PPS.

An elastic partly slotted blade 4 made of a long fibre-reinforced thermoset or thermoplastic composite including 40% to 65% volume fraction of fibres which are preferably longer than 50 mm, the fibres being preferably carbon fibres, glass fibres, aramid or basalt fibres. The composite matrix may be either a thermoset polymer (epoxy, polyester, vinyl ester) or a thermoplastic one (PE, PA, PP, PEI, PEKK, PET, PI, ABS, POM, PMMA). The thermoset composite can be processed by wet layup, vacuum bagging, autoclave, compression moulding or resin transfer moulding. Thermoplastic composites can be processed by compression moulding, resin transfer moulding or any other suitable process.

Figure 2:
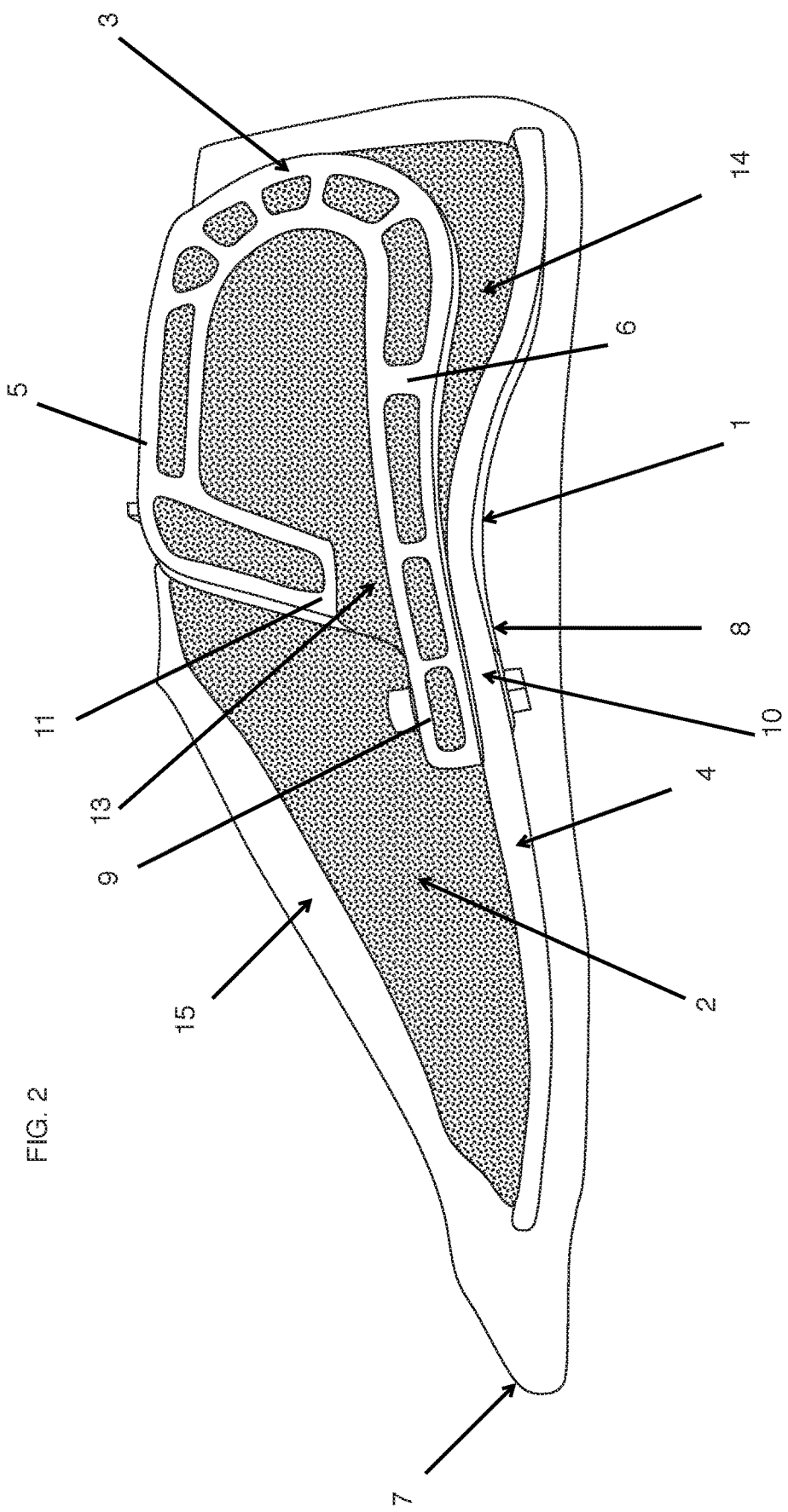
FIG. 2 shows a complete prosthetic foot (cross-sectional view) that includes the keel of FIG. 1.

In the illustrated example (see FIG. 2), the keel 1 is embedded in an encapsulation material 2 and both objects 1,2 being contained within a shell 15 having the shape of a normal foot.

The ankle 3 has roughly a horizontal U-shape with an upper branch 5 and a longer lower branch 6. The upper branch 5 has a vertical extension 11 that forms a part of an overload protection system that will be described below.

The free end 9 of the lower branch 6 is fixed to the blade central area 10.

In the illustrated example, bolts are used for the fixation, but any other suitable fixation means may be used.

The foot prosthesis, by combination of the elastic ankle 3 and elastic blade 4, features biomechanical movements (plantar, dorsiflexion, inversion, eversion) and heel shock absorption thanks to their elastic behaviour and a longitudinal slit in the two parts.

As mentioned previously, ankle 3 and 4 are slotted, i.e. they contain a longitudinal slot.

Such slots increase the flexibility of the objects. The invention is of course not limited to such a configuration. Slots are not mandatory. Any other way to increase the flexibility could also be used.

The foot prosthesis features energy storage and release (a.k.a. ESAR in the prosthetics jargon) with an efficiency above 85%, said energy storage and release taking part in similar proportions in both parts.

The ankle 3 and heel 12 areas may include overload protection systems to prevent damage of the prosthetic foot in case of severe loading during use, the overload protection systems being based on a blocking mechanism during plantar and dorsiflexion, the blocking mechanism using a spacer, made e.g. of an elastomeric foam (thermoset or thermoplastic) with a specific and controlled compaction point. The spacer may be made from the same material as the encapsulation material 2. In this latter case, the spacer material has a higher density than the density of the surrounding encapsulation material. The spacers are preferably in an area 13 that is located between the vertical extension 11 and the blade central area 10 or in an area 14 that is located between the ankle 3 rear part and the blade 4.

The low-density foam is encapsulated in a high-density polymer foam (typically >0.7 g/cm$^3$), the foam being thermoset or thermoplastic and is used as an external shell to protect internal parts. This external shell has the proportions and aspect of a human foot (with or without a split between the big toe and others).

Typical Shore hardness of used foams ranges from 35 Shore A to 70 Shore A.

The invention is of course not limited to the illustrated example.

The invention claimed is:

1. A prosthetic foot having a bottom and comprising a keel embedded in an encapsulation material;
    said keel comprising two separate elements that are fixed to each other, namely:
        a horizontal U-shaped elastic ankle oriented in a way as having an upper branch of said U and a lower branch of said U pointed towards the forefoot,
        an elastic blade that extends along the foot bottom;
    wherein a free extremity of the lower branch of said U is fixed to a central area of the elastic blade,
    wherein the ankle is made of an injection-moulded long fibre thermoplastic (LFT) composite, and
    wherein said long fibre thermoplastic (LFT) composite comprises 15% to 70% volume fraction of fibres with a length ranging from 1 mm to 15 mm.

2. The prosthetic foot according to claim 1 wherein the lower branch of said U is longer than the upper branch of said U.

3. The prosthetic foot according to claim 1 wherein said elastic blade is made of a composite that comprises 40% to 65% volume fraction of fibres which are longer than 50 mm.

4. The prosthetic foot according to claim 1 including an overload protection system to prevent damage of the prosthetic foot in case of severe loading during use.

5. The prosthetic foot according to claim 4 wherein said protection system comprises a spacer that is arranged in at least one area that is located between two overlapping parts of the keel.

6. The prosthetic foot according to claim 4 wherein said protection system comprises a vertical element that forms an extension of the ankle upper branch.

7. The prosthetic foot according to claim 6 wherein said spacer is arranged in an area that is located between the vertical element and the blade central area.

8. The prosthetic foot according to claim 5 comprising another spacer that is arranged in an area that is located between a rear part of the ankle and the blade.

9. The prosthetic foot according to claim 5, wherein the spacer is made of a different material than said encapsulation material.

10. The prosthetic foot according to claim 5, wherein the spacer is made of the encapsulation material but said material has a higher density than the density of the surrounding encapsulation material.

11. A prosthetic foot having a bottom and comprising a keel embedded in an encapsulation material;
    said keel comprising two separate elements that are fixed to each other, namely:
        a horizontal U-shaped elastic ankle oriented in a way as having an upper branch of said U and a lower branch of said U pointed towards the forefoot,
        an elastic blade that extends along the foot bottom;
    wherein a free extremity of the lower branch of said U is fixed to a central area of the elastic blade,
    wherein the ankle is made of an injection-moulded long fibre thermoplastic (LFT) composite, and
    wherein said elastic blade is made of a composite that comprises 40% to 65% volume fraction of fibres which are longer than 50 mm.

12. The prosthetic foot according to claim 11 wherein the lower branch of said U is longer than the upper branch of said U.

13. The prosthetic foot according to claim 11 wherein said long fibre thermoplastic (LFT) composite comprises 15% to 70% volume fraction of fibres with a length ranging from 1 mm to 15 mm.

14. The prosthetic foot according to claim 11 including an overload protection system to prevent damage of the prosthetic foot in case of severe loading during use.

15. The prosthetic foot according to claim 14 wherein said protection system comprises a spacer that is arranged in at least one area that is located between two overlapping parts of the keel.

16. The prosthetic foot according to claim 14 wherein said protection system comprises a vertical element that forms an extension of the ankle upper branch.

17. The prosthetic foot according to claim 16 wherein said spacer is arranged in an area that is located between the vertical element and the blade central area.

18. The prosthetic foot according to claim 15 comprising another spacer that is arranged in an area that is located between a rear part of the ankle and the blade.

19. The prosthetic foot according to claim 15, wherein the spacer is made of a different material than said encapsulation material.

20. The prosthetic foot according to claim 15, wherein the spacer is made of the encapsulation material but said material has a higher density than the density of the surrounding encapsulation material.

* * * * *